United States Patent
Terranova et al.

[11] Patent Number: 5,876,465
[45] Date of Patent: Mar. 2, 1999

[54] COMPOSITIONS FOR DYEING KERATIN FIBRES CONTAINING 2-IMINOINDOLINE DERIVATIVES AND DYEING PROCESS

[75] Inventors: Eric Terranova, Asnieres; Aziz Fadli, Le Blanc Mesnil; Alain Lagrange, Coupvray, all of France

[73] Assignee: L'Oreal, Paris, France

[21] Appl. No.: 916,407

[22] Filed: Aug. 22, 1997

[30] Foreign Application Priority Data

Aug. 23, 1996 [FR] France ................... 96 10413

[51] Int. Cl.⁶ .......................................... A61K 7/13
[52] U.S. Cl. ........................... 8/409; 8/408; 8/423; 8/574
[58] Field of Search ............... 8/406, 408, 409, 8/410, 416, 421, 423, 574, 407

[56] References Cited

U.S. PATENT DOCUMENTS

| | | | |
|---|---|---|---|
| 3,000,899 | 9/1961 | Hoffmann et al. | 260/319 |
| 3,944,672 | 3/1976 | Steinman | 424/274 |
| 3,984,563 | 10/1976 | Winters | 424/274 |
| 4,620,850 | 11/1986 | Bachmann et al. | 8/423 |
| 4,776,857 | 10/1988 | Carroll et al. | 8/409 |
| 4,932,977 | 6/1990 | Schultz | 8/423 |
| 5,021,067 | 6/1991 | Grollier | 8/409 |
| 5,053,053 | 10/1991 | De Labbey et al. | 8/423 |
| 5,096,455 | 3/1992 | Grollier | 8/409 |
| 5,167,669 | 12/1992 | Grollier | 8/409 |
| 5,496,543 | 3/1996 | Lagrange et al. | 424/70.7 |
| 5,583,234 | 12/1996 | Lagrange et al. | 548/455 |
| 5,609,649 | 3/1997 | Junino et al. | 8/409 |
| 5,752,982 | 5/1998 | Lang et al. | 8/409 |

FOREIGN PATENT DOCUMENTS

| | | |
|---|---|---|
| 0 376 776 | 7/1990 | European Pat. Off. |
| 0 428 441 | 5/1991 | European Pat. Off. |
| 2 008 797 | 1/1970 | France . |
| 24 42 667 | 3/1975 | Germany . |
| 1 217 479 | 12/1970 | United Kingdom . |
| WO 92 17157 | 10/1992 | WIPO . |
| WO 93 13744 | 7/1993 | WIPO . |
| WO 93 13745 | 7/1993 | WIPO . |

OTHER PUBLICATIONS

Chemical Abtracts, vol. 79, No. 9, 1973 (abstract No. 53260x), Portnov et al.
Chemical Abstracts, vol. 78, No. 11, 1973 (abstract No. 71606y), Harmon et al.
Chemical Abstracts, vol. 87, No. 25, Dec. 19, 1977 (abstract No. 201378z), Sagitullin et al.
Chemical Abstracts, vol. 94, No. 13, Mar. 30, 1981 (abstract No. 103110f), Kost et al.
Chemical Abstracts, vol. 75, No. 23, Dec. 6, 1971 (abstract No. 140696e), Gorbunova et al.
Chemical Abstracts, vol. 74, No. 25, Jun. 21, 1971 (abstract No. 141438p), Hino et al.
Chemical Abstracts, vol. 73, No. 15, Oct. 12, 1970 (abstract No. 76975z), Sagitullin et al.
Chemical Abstracts, vol. 88, No. 17, Apr. 24, 1978 (abstract No. 121064z), Balli et al.
Chemical Abstracts, vol. 73, No. 9, Aug. 31, 1970 (abstract No. 45252g), Hino et al.
Chemical Abstracts, vol. 68, No. 23, Jun. 3, 1968 (abstract No. 105143f), Glushkov et al.
Chemical Abtracts, vol. 79, No. 5, Aug. 6, 1973 (abstract No. 31782s), Golubeva et al.
Chemical Abstracts, vol. 93, No. 11, Sep. 15, 1980 (abstract No. 114247m), Kost et al.
Chemical Abstracts, vol. 90, No. 21, May 21, 1979 (abstract No. 168410r), Hiremath et al.
Chemical Abstracts, vol. 114, No. 13, Apr. 1, 1991 (abstract No. 121938t), Portnov et al.
Chemical Abstracts, vol. 82, No. 23, Jun. 9, 1975 (abstract No. 156003g), Gilchrist et al.
Chemical Abstracts, vol. 80, No. 17, Apr. 29, 1974 (abstract No. 95788b), Abramenko.
Chemical Abstracts, vol. 108, No. 5, Feb. 1, 1988 (abstract No. 37569s), Portnov et al.
Chemical Abstracts, vol. 107, No. 10, Sep. 7, 1987 (abstract No. 88896h), Obtemperanskaya et al.
Chemical Abstracts, vol. 119, No. 3, Jul. 19, 1993 (abstract No. 27959g), Fernandez Garcia et al.
Chemical Abstracts, vol. 123, No. 1, Jul. 3, 1995 (abstract No. 252s), Fernandez Garcia et al.

*Primary Examiner*—Paul Lieberman
*Assistant Examiner*—Caroline D. Liott
*Attorney, Agent, or Firm*—Finnegan, Henderson, Farabow, Garrett & Dunner, L.L.P.

[57] ABSTRACT

A composition for dyeing keratin fibres, and in particular human keratin fibres such as the hair, characterized in that it comprises, in a medium which is suitable for dyeing:

at least one coupler selected from 2-iminoindoline derivatives of formula (I) and acid addition salts thereof:

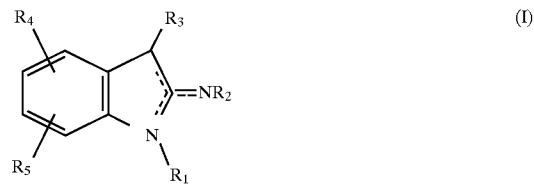

in which:

$R_1$ represents hydrogen, alkyl, hydroxyalkyl, alkoxycarbonyl or acyl;

$R_2$ represents hydrogen, alkyl, phenyl or arylsulphonyl;

$R_3$ represents hydrogen or alkyl which may be substituted with one or more hydroxyl, alkoxy, amino, alkylamino, dialkylamino, cyano or aryl groups;

$R_4$ and $R_5$, which may be identical or different, denote hydrogen, hydroxyl, alkyl, alkoxy, amino, alkylamino, dialkylamino, aralkyl, halogen or a nitro group; and at least one oxidation base.

33 Claims, No Drawings

COMPOSITIONS FOR DYEING KERATIN FIBRES CONTAINING 2-IMINOINDOLINE DERIVATIVES AND DYEING PROCESS

The invention relates to a composition for the oxidation dyeing of keratin fibres, containing at least one 2-iminoindoline derivative as coupler and at least one oxidation base.

It is known to dye keratin fibres, and in particular human hair, with dye compositions containing oxidation dye precursors, in particular ortho- or para-phenylenediamines, ortho- or para-aminophenols, or heterocyclic compounds, which are generally referred to as oxidation bases. The oxidation dye precursors, or oxidation bases, are colourless or weakly coloured compounds which, when combined with oxidizing products, may give rise to coloured compounds and dyes by a process of oxidative condensation.

It is also known that the shades obtained with these oxidation bases may be varied by combining them with couplers or coloration modifiers, it being possible for the latter to be chosen in particular from aromatic meta-diamines, meta-aminophenols, meta-diphenols and certain heterocyclic compounds such as indole compounds.

The variety of molecules used as oxidation bases and couplers makes it possible to obtain a wide range of colours.

The so-called "permanent" coloration obtained by means of these oxidation dyes seeks to satisfy a certain number of requirements. Thus, it is desired to have no toxicological drawbacks and to allow shades of the desired intensity to be obtained and to have good resistance to external agents (light, bad weather, washing, permanent-waving, perspiration and rubbing).

It is also desired that the dyes allow white hairs to be covered and, lastly, to be as unselective as possible, that is to say to allow the smallest possible differences in coloration to be produced over the entire length of the same keratin fibre, which may indeed be differently sensitized (i.e. damaged) between its tip and its root.

Now, the inventors have discovered that it is possible to obtain powerful new dyes by using specific 2-iminoindoline derivatives, these dyes being relatively unselective, particularly fast, and capable of giving rise to intense colorations in varied shades. These compounds (for the part which is novel per se) are moreover readily synthesized.

This discovery forms the basis of the present invention.

The subject of the invention is thus a composition for dyeing keratin fibres, and in particular human keratin fibres such as the hair, characterized in that it comprises, preferably in a medium which is suitable for dyeing:

at least one coupler selected from 2-iminoindoline derivatives of formula (I) and acid addition salts thereof:

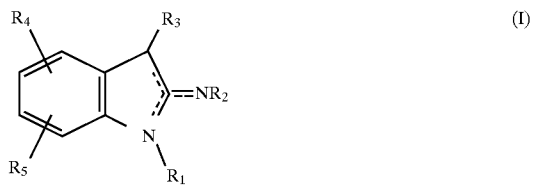

in which:

$R_1$ represents a hydrogen atom, a $C_1$–$C_4$ alkyl, $C_1$–$C_4$ monohydroxyalkyl, $C_2$–$C_4$ polyhydroxyalkyl or ($C_1$–$C_4$)alkoxycarbonyl radical or a $C_2$–$C_4$ acyl radical;

$R_2$ represents a hydrogen atom or a $C_1$–$C_4$ alkyl, phenyl or arylsulphonyl radical;

$R_3$ represents a hydrogen atom or a $C_1$–$C_4$ alkyl radical which may be substituted with one or more hydroxyl, $C_1$–$C_4$ alkoxy, amino, mono($C_1$–$C_4$)alkylamino, di($C_1$–$C_4$)alkylamino, cyano or aryl groups;

$R_4$ and $R_5$, which may be identical or different, denote a hydrogen atom or a hydroxyl, $C_1$–$C_4$ alkyl, $C_1$–$C_4$ alkoxy, amino, mono($C_1$–$C_4$)alkylamino, di($C_1$–$C_4$) alkylamino or $C_7$–$C_{11}$ aralkyl radical, a halogen atom or a nitro group;

and at least one oxidation base.

In formula (I) above, the $C_1$–$C_4$ alkyl and $C_1$–$C_4$ alkoxy groups may be linear or branched, and among the halogen atoms, mention may be made of chlorine, bromine, iodine and fluorine.

In formula (I) above, the aryl groups may denote, for example, phenyl, thiophene or furan.

Formula (I) as defined above may give rise to the following three tautomeric forms:

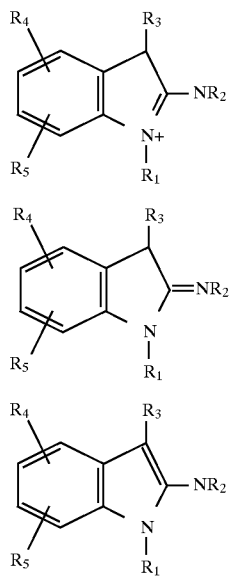

The preponderance and/or stability of each of these three tautomeric forms will depend upon the nature of the substituents $R_1$, $R_2$ and $R_3$.

For the sake of clarity, the compounds derived from the 2-iminoindole of the invention will be defined by the following tautomeric form:

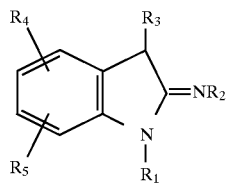

The colorations obtained with the dye composition in accordance with the invention are varied shades which can be powerful, relatively unselective and have excellent properties of fastness both to atmospheric agents such as light and bad weather and to perspiration and the various treatments to which the hair may be subjected (shampooing, permanent waving).

Among the 2-iminoindoline derivatives of formula (I) which may be used as couplers in the compositions in accordance with the invention, mention may be made in particular of:

4-benzyloxy-1,3-dihydroindol-2-ylideneamine, 4-methoxy-1,3-dihydroindol-2-ylideneamine, 2-imino-2,3-dihydro-1H-indol-4-ol, 5-chloro-7-methoxy-1,3-dihydroindol-2-ylideneamine, 5,6-dimethoxy-1,3-dihydroindol-2-ylideneamine, 5,6-dihydroxy-1,3-dihydroindol-2-ylideneamine, 1,3-dihydroindol-2-ylideneamine, 2-imino-2,3-dihydro-1H-indole-5,6-diol, as well as the addition salts thereof with an acid.

The 2-iminoindoline derivative(s) of formula (I) preferably represent from 0.0005 to 12% by weight approximately relative to the total weight of the dye composition, and even more preferably from 0.005 to 6% by weight approximately relative to this weight.

The nature of the oxidation base(s) which may be used in the dye composition according to the invention is not critical. This or these oxidation base(s) is (are) preferably chosen from para-phenylenediamines, bis(phenyl)alkylenediamines, para-aminophenols, ortho-aminophenols and heterocyclic bases, and the addition salts thereof with an acid.

Among the para-phenylenediamines which may be used as oxidation bases in the dye composition according to the invention, mention may be made in particular of the compounds corresponding to formula (II) below and the addition salts thereof with an acid:

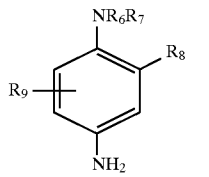

in which:

$R_6$ represents a hydrogen atom or a $C_1$–$C_4$ alkyl, $C_1$–$C_4$ monohydroxyalkyl, $C_2$–$C_4$ polyhydroxyalkyl or $(C_1$–$C_4)$alkoxy$(C_1$–$C_4)$alkyl radical, $R_7$ represents a hydrogen atom or a $C_1$–$C_4$ alkyl, $C_1$–$C_4$ monohydroxyalkyl or $C_2$–$C_4$ polyhydroxyalkyl radical, $R_8$ represents a hydrogen atom, a halogen atom such as a chlorine atom or a $C_1$–$C_4$ alkyl, sulpho, carboxyl, $C_1$–$C_4$ monohydroxyalkyl or $C_1$–$C_4$ hydroxyalkoxy radical, $R_9$ represents a hydrogen atom or a $C_1$–$C_4$ alkyl radical.

In formula (II) above, and when $R_8$ is other than a hydrogen atom, then $R_6$ and $R_7$ preferably represent a hydrogen atom and $R_8$ is preferably identical to $R_9$, and when $R_8$ represents a halogen atom, then $R_6$, $R_7$ and $R_9$ preferably represent a hydrogen atom.

Among the para-phenylenediamines of formula (II) above, mention may be made more particularly of para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-(β-methoxyethyl)amino-benzene and 2-chloro-para-phenylenediamine, and the addition salts thereof with an acid.

Among the bis(phenyl)alkylenediamines which may be used as oxidation bases in the dye composition according to the invention, mention may be made in particular of the compounds corresponding to formula (III) below, and the addition salts thereof with an acid:

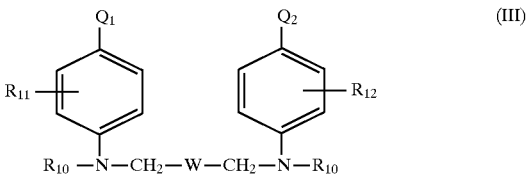

in which:

$Q_1$ and $Q_2$, which may be identical or different, represent a hydroxyl radical or a radical $NHR_{13}$ in which $R_{13}$ represents a hydrogen atom or a $C_1$–$C_4$ alkyl radical, $R_{10}$ represents a hydrogen atom or a $C_1$–$C_4$ alkyl, $C_1$–$C_4$-monohydroxyalkyl or $C_2$–$C_4$ polyhydroxyalkyl radical or a $C_1$–$C_4$ aminoalkyl radical in which the amino residue may be substituted, $R_{11}$ and $R_{12}$, which may be identical or different, represent a hydrogen or halogen atom or a $C_1$–$C_4$ alkyl radical, W represents a radical taken from the group comprising the following radicals:

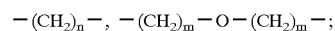
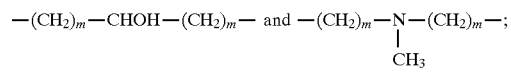

in which n is an integer ranging from 0 and 8 and m is an integer ranging from 0 to 4.

Among the bis(phenyl)alkylenediamines of formula (III) above, mention may be made more particularly of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid is particularly preferred.

Among the para-aminophenols which may be used as oxidation bases in the dye composition according to the invention, mention may be made in particular of the compounds corresponding to formula (IV) below, and the addition salts thereof with an acid:

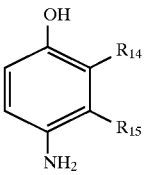

in which:

$R_{14}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical, $R_{15}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$ alkoxy$(C_1$–$C_4)$alkyl radical, it being understood that at least one of the radicals $R_{13}$ or $R_{14}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which may be used as oxidation bases in the dye composition according to the invention, mention may be made in particular of 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases which may be used as oxidation bases in the dye composition according to the invention, mention may be made in particular of pyridine derivatives, pyrimidine derivatives and pyrazole derivatives, and the addition salts thereof with an acid.

Among the pyridine derivatives, mention may be made more particularly of the compounds described, for example, in patents GB 1,026,978 and GB 1,153,196 (the disclosures of which are specifically incorporated by reference herein), such as 2,5-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-333,495 (the disclosures of which are specifically incorporated by reference herein), such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE 3,843,892 and DE 4,133,957 and patent applications WO 94/08969 and WO 94/08970 (the disclosures of which are specifically incorporated by reference herein), such as 4,5-diamino-1-methylpyrazole, 3,4-diaminopyrazole, and the addition salts thereof with an acid.

According to the invention, the oxidation base or bases preferably represent from 0.0005 to 12% by weight approximately relative to the total weight of the dye composition, and even more preferably from 0.005 to 6% by weight approximately relative to this weight.

The dye composition according to the invention may also contain one or more additional couplers other than the 2-iminoindoline derivatives of formula (I) and/or one or more direct dyes so as to vary or enrich with glints the shades obtained with the oxidation bases.

The additional couplers which may be used in the composition according to the invention may be chosen from the couplers used conventionally in oxidation dyeing and among which mention may be made in particular of meta-phenylenediamines, meta-aminophenols, meta-diphenols and heterocyclic couplers such as, for example, indole derivatives and indoline derivatives, and the addition salts thereof with an acid.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindoline, and the addition salts thereof with an acid.

When they are present, these additional couplers preferably represent from 0.0005 to 5% by weight approximately relative to the total weight of the dye composition, and even more preferably from 0.005 to 3% by weight approximately relative to this weight.

The addition salts with an acid of the oxidation base(s) and/or of the additional couplers which may be used in the dye composition of the invention are chosen in particular from the hydrochlorides, hydrobromides, sulphates, tartrates, lactates and acetates.

The medium which is suitable for dyeing (or the support) generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents may be present in proportions preferably from approximately 1 to 40% by weight relative to the total weight of the dye composition, and even more preferably from approximately 5 to 30% by weight.

The pH of the dye composition in accordance with the invention generally ranges from 3 to 12. It may be adjusted to the desired value using acidifying or basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of formula (V) below:

in which R is a propylene residue optionally substituted with a hydroxyl group or a $C_1$–$C_4$ alkyl radical; $R_{16}$, $R_{17}$, $R_{18}$ and $R_{19}$, which may be identical or different, represent a hydrogen atom or a $C_1$–$C_4$ alkyl or $C_1$–$C_4$ hydroxyalkyl radical.

The dye composition according to the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifying agents.

A person skilled in the art should take care to select the optional complementary compound(s) mentioned above such that the advantageous properties intrinsically associated with the dye composition in accordance with the invention are not, or are not substantially, adversely affected by the addition or additions envisaged.

The dye composition according to the invention may be in various forms, such as in the form of liquids, creams, gels or any other form which is suitable for dyeing keratin fibres, and in particular human hair.

The subject of the invention is also the use of the 2-iminoindoline derivatives of formula (I) above, as coupler, in combination with at least one oxidation base for the oxidation dyeing of keratin fibres, and in particular human keratin fibres such as the hair.

Another subject of the invention is a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added only at the time of use to the dye composition or which is present in an oxidizing composition that is applied simultaneously or sequentially in a separate manner.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place preferably for 3 to 50 minutes approximately, more preferably 5 to 30 minutes approximately, after which the fibres are rinsed, washed with shampoo, rinsed again and dried.

The oxidizing agent present in the oxidizing composition as defined above may be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably varies approximately from 3 to 12 and even more preferably from 5 to 11. It is adjusted to the desired value using acidifying or basifying agents usually used in the dyeing of keratin fibres and as are defined above.

The oxidizing composition as defined above may also include various adjuvants used conventionally in compositions for dyeing the hair and as are defined above.

The composition which is finally applied to the keratin fibres may be in various forms, such as in the form of liquids, creams, gels or any other form which is suitable for dyeing keratin fibres, and in particular human hair.

Another subject of the invention is a multi-compartment device for dyeing or dyeing "kit" or any other multi-compartment packaging system a first compartment of which contains the dye composition as defined above and a second compartment of which contains the oxidizing composition as defined above. These devices may be equipped with a means which makes it possible to deliver the desired mixture onto the hair, such as the devices described in patent FR-2,586,913, the disclosure of which is specifically incorporated by reference herein.

Compounds of formula (I), used as couplers in the context of the present invention, are either known or novel compounds.

The specific compounds of formula (IA) corresponding to formula (I) in which $R_1$ and $R_2$ are hydrogen atoms may be obtained according to a preparation process described in RG Glushkov documents USSR Patent 179 320 (1965) and Chem. Abstr 65, 2225 (1966), and corresponding to Scheme A below:

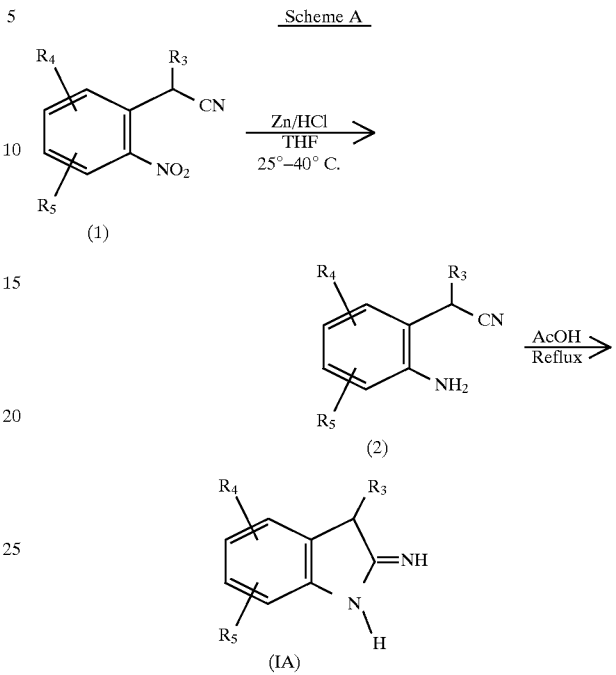

In Scheme A defined above, the meanings of the radicals $R_3$, $R_4$ and $R_5$ in formulae (1) and (2) are identical to those indicated above in formula (I).

This is a two-step process using starting compounds of formula (1) having the ortho-nitrophenylacetonitrile structure whose preparation method is known in the literature (M. Makosza, J. Winiarski, Acc. Chem. Res., 87,1987, 282; M. Makosza, W. Danikiewicz, K. Wojciechowski, Liebigs, Ann. Chem., 1988, 203).

The first step is either a chemical reduction in the presence of an organic solvent using metals such as zinc or tin, or a selective hydrogenation using a catalyst such as palladium or platinum. It leads to derivatives of ortho-aminophenylacetonitrile structure (formula (2)). Zinc powder in hydrochloric acid medium is more particularly used for this reaction. The solvents used are preferably ethers and more particularly tetrahydrofuran (THF). The reaction temperature ranges preferably from 25° C. to the reflux temperature of the solvent and more particularly from 25° to 40° C.

The second step is a cyclization reaction in acidic medium in the presence of an organic solvent. Acetic acid is more particularly used. The reaction temperature is that of reflux of the solvent. The final product of formula (I) is preferably isolated in the form of the addition salt with an acid, preferably in the form of hydrochloride. It is obtained by precipitation of the reaction medium in acidic medium, for example, in order to obtain a hydrochloride, a stream of HCl gas is passed through at the end of the reaction.

The specific compounds of formula (IB) corresponding to formula (I) in which $R_1$ is a hydrogen atom and $R_2$ is other than a hydrogen atom, and the specific compounds of formula (IC) corresponding to formula (I) in which $R_1$ and $R_2$ are both other than a hydrogen atom, may be obtained according to a preparation process with reference to the literature, corresponding to Scheme B below:

Scheme B

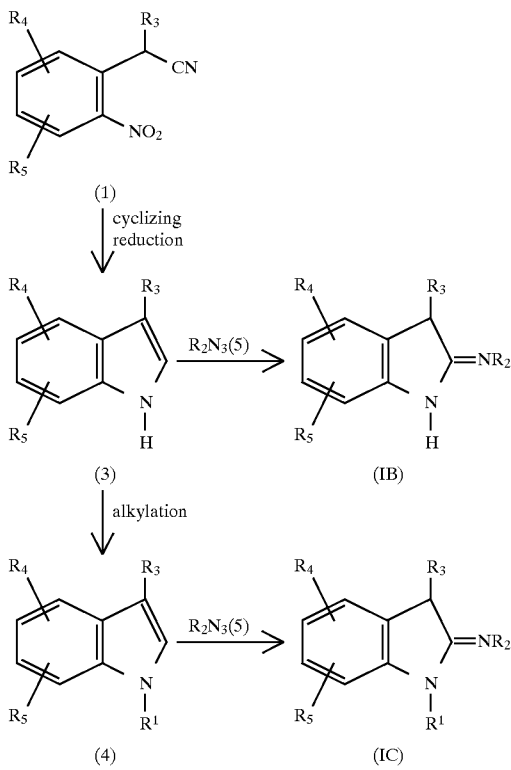

Compound (1) may be treated under cyclizing reduction conditions according to known methods, such as, for example, that described by Makosza M. et al. in Liebigs Ann. Chem., 203, (1988) in order to lead to the indole (3).

The indole (3) may be alkylated to lead to the indole (4) according to standard methods described in "Heterocyclic compounds: Indoles" part II p. 72–73, edited by N.J. Houlian, Wiley-Interscience.

Compounds (3) and (4) may react with an azide of structure (5) in order to lead respectively to the 2-iminoindolines (IB) and (IC) according to a method which has already been described [Harmon R. E. et al., J. Org. Chem. 38(1), 11, (1973)].

The compounds of structures (IB) and (IC) may also be obtained by reaction of an amine $R_2NH_2$ with a 2-indolinethione derivative of structure (6) and (7) respectively, as described by Hino T. et al. in Tetrahedron 27, 775, (1971) and represented in Scheme C below:

Scheme C

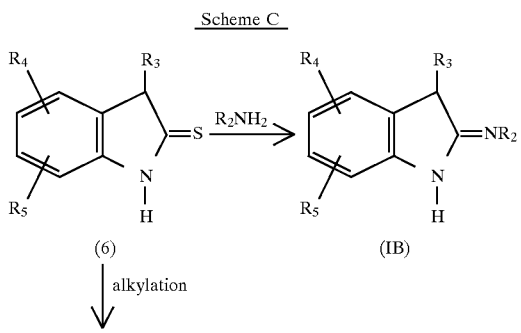

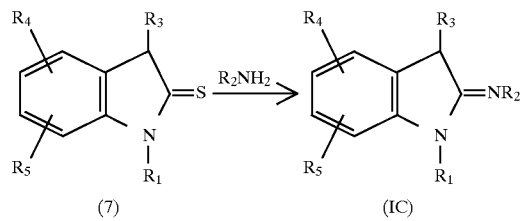

The examples which follow are intended to illustrate the invention without, however, limiting the scope thereof.

PREPARATION EXAMPLES

Example No. 1: Preparation of 1,3-dihydroindol-2-ylideneamine hydrochloride

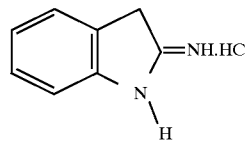

2 g of (2-nitrophenyl)acetonitrile were dissolved in a 10 mil/10 ml mixture of THF/37% HCl in a 50 ml three-necked round-bottomed flask fitted with a thermometer and a condenser.

5 grams of zinc were introduced portionwise at a temperature below 40° C. After complete addition, stirring was maintained for 15 minutes and the excess zinc was filtered off. The filtrate was evaporated to dryness. The (2-aminophenyl)acetonitrile hydrochloride was taken up in 25 ml of refluxing acetic acid. After heating for one hour, the solution was saturated with hydrogen chloride gas. The precipitate was filtered off. It was dried under vacuum over phosphorus pentoxide and potassium hydroxide. 1 g of 1,3-dihydroindol-2-ylideneamine hydrochloride was obtained (yield=48%).

$^1$H and $^{13}$C NMR in accordance with the structure.
$^1$H NMR (DMSO-$d_6$; 400 MHz)

| δ (ppm) | multiplicity | integration |
|---|---|---|
| 4.19 | s | 2 |
| 7.13 | ddd | 1 |
| 7.22 | d | 1 |
| 7.30 | ddd | 1 |
| 7.41 | d | 1 |
| 9.95–10.21 | 2 broad s | 2 |
| 12.42 | broad s | 1 |

Example No. 2: Preparation of 4-methoxy-1,3-dihydroindol-2-ylideneamine hydrochloride

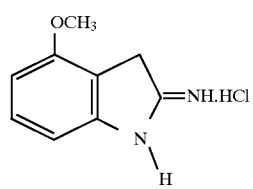

1st step: Preparation of (2-amino-6-methoxyphenyl)acetonitrile hydrochloride 3.84 g of (2-methoxy-6-nitrophenyl)aceto-nitrile were dissolved in a 1/1 mixture of THF/HCl (40 ml) in a 100 ml three-necked round-bottomed flask fitted with a thermometer and a condenser.

7.8 g of zinc were introduced portionwise at a temperature below 40° C. After complete addition, the stirring was maintained for 15 minutes and the excess zinc was then filtered off. The filtrate was evaporated to dryness. 3 g of (2-amino-6-methoxyphenyl)aceto-nitrile hydrochloride were recovered (yield=75%).

2nd step: Preparation of 4-methoxy- 1,3-dihydroindol-2-ylideneamine hydrochloride 3 g of (2-amino-6-methoxyphenyl)acetonitrile hydrochloride in 25 ml of acetic acid were maintained at reflux for one hour in a 100 ml three-necked round-bottomed flask fitted with a thermometer and a condenser. After evaporation of the acid under vacuum, 2.9 g of 4-methoxy-1,3-dihydroindol-2-ylideneamine hydrochloride were recovered after drying under vacuum over phosphorus pentoxide and potassium hydroxide (yield=96%).

$^1$H and $^{13}$C NMR in accordance with the structure.

$^1$H NMR (DMSO-d$_6$; 400 MHz)

| δ (ppm)    | multiplicity  | integration |
|------------|---------------|-------------|
| 3.84       | s             | 3           |
| 4.06       | s             | 2           |
| 6.80–6.83  | 2 d           | 2           |
| 7.31       | t             | 1           |
| 9.72–9.98  | 2s            | 2           |
| 12.09      | s             | 1           |

Example No. 3: Preparation of 2-imino-2,3-dihydro-1H-indol-4-ol hydrobromide

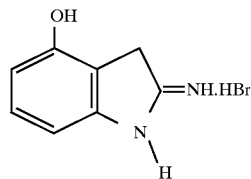

2 g of 4-methoxy-1,3-dihydroindol-2-ylideneamine hydrochloride in 8 ml of 60% hydrobromic acid were maintained at reflux for four hours in a 25 ml three-necked round-bottomed flask equipped with a thermometer and a condenser. The medium was left to return to room temperature. The 2-imino-2,3-dihydro-1H-indol-4-ol hydrobromide crystallized out. It was filtered off and washed with petroleum ether. 1.6 g of product were recovered after drying under vacuum over phosphorus pentoxide and potassium hydroxide (yield=70%).

$^1$H and $^{13}$C NMR in accordance with the structure.

$^1$H NMR (DMSO-d$_6$; 400 MHz)

| δ (ppm)    | multiplicity   | integration |
|------------|----------------|-------------|
| 4.02       | s              | 2           |
| 6.60–6.67  | 2 d            | 2           |
| 7.13       | t              | 1           |
| 9.64–9.95  | 2s + broad s   | 3           |
| 11.98      | s              | 1           |

Example No. 4: Preparation of 4-benzyloxy-1,3-dihydroindol-2-ylideneamine hydrochloride

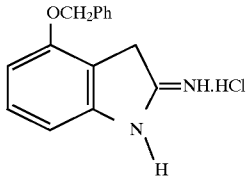

1st step: Preparation of (2-amino-6-benzyloxyphenyl)-acetonitrile 135 g of (2-benzyloxy-6-nitrophenyl)aceto-nitrile were dissolved in 1 liter of THF and 0.5 liter of 37% hydrochloric acid in a 2 liter SLV reactor equipped with a condenser and a thermometer.

150 g of zinc were introduced portionwise at a temperature below 40° C. After complete addition, the stirring was maintained for 15 minutes and the excess zinc was then filtered off.

The filtrate was poured onto 10 volumes of ice-water. The precipitate was filtered off and washed with water and with petroleum ether. 80 g of (2-amino-6-benzyloxyphenyl)acetonitrile were recovered after drying under vacuum and over phosphorus pentoxide (yield=67%).

2nd step: Preparation of 4-benzyloxy-1,3-dihydroindol-2-ylideneamine hydrochloride 71.5 g of (2-amino-6-benzyloxyphenyl)aceto-nitrile in 350 ml of acetic acid were maintained at reflux for one hour in a 500 ml three-necked round-bottomed flask fitted with a thermometer and a condenser. The medium was allowed to return to room temperature and was then saturated with hydrogen chloride gas. The precipitate was filtered off. It was washed with petroleum ether. 63 g of 4-benzyloxy-1,3-dihydroindol-2-ylideneamine hydrochloride were recovered after drying under vacuum over phosphorus pentoxide and potassium hydroxide (yield=76%).

$^1$H and $^{13}$C NMR in accordance with the structure.

$^1$-H NMR (DMSO-d$_6$; 400 MHz)

| δ (ppm)      | multiplicity | integration |
|--------------|--------------|-------------|
| 4.10         | s            | 2           |
| 5.20         | s            | 2           |
| 6.87         | d            | 2           |
| 7.26         | t            | 1           |
| 7.34         | m            | 1           |
| 7.39         | m            | 2           |
| 7.46         | m            | 2           |
| 10.04–10.38  | 2s           | 2           |
| 12.51        | s            | 1           |

Example No. 5: Preparation of 5-chloro-7-methoxy-1,3-dihydroindol-2-ylideneamine hydrochloride

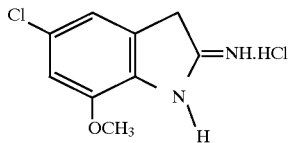

1st step: Preparation of (2-amino-5-chloro-3-methoxyphenyl)acetonitrile

In accordance with Example No. 3, 22.7 g of (5-chloro-3-methoxy-2-nitrophenyl)acetonitrile dissolved in a 100 ml/70 ml mixture of THF/37% HCl were reduced with 26 g of zinc powder. 19 g of (2-amino-5-chloro-3-methoxyphenyl)acetonitrile were obtained (yield=97%).

2nd step: Preparation of 5-chloro-7-methoxy-1,3-dihydroindol-2-ylideneamine hydrochloride In accordance with Example No. 3, 15 g of (2-amino-5-chloro-3-methoxyphenyl)acetonitrile were brought to reflux in 150 ml of acetic acid. 11.2 g of 5-chloro-7-methoxy-1,3-dihydroindol-2-ylideneamine hydrochloride were obtained (yield=63.6%).

$^1$H and $^{13}$C NMR in accordance with the structure.

$^1$H NMR (DMSO-$d_6$; 400 MHz)

| δ (ppm) | multiplicity | integration |
|---|---|---|
| 3.91 | s | 3 |
| 4.23 | s | 2 |
| 7.13 | d | 1 |
| 7.16 | d | 1 |
| 9.13–10.05 | 2s | 2 |
| 12.51 | s | 1 |

Example No. 6: Preparation of 5,6-dimethoxy-1,3-dihydroindol-2-ylideneamine hydrochloride

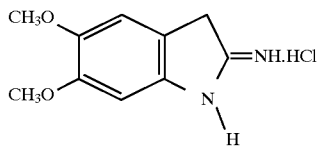

22.2 g of (4,5-dimethoxy-2-nitrophenyl)aceto-nitrile were dissolved in a 150 ml/60 ml mixture of THF/37% HCl in a 250 ml three-necked round-bottomed flask fitted with a thermometer and a condenser.

26 g of zinc powder were introduced portionwise at a temperature below 40° C. The addition was exothermic. After complete addition, the stirring was maintained for 15 minutes and the excess zinc was then filtered off. The filtrate was saturated with HCl gas and the precipitate obtained was then filtered off. It was washed with petroleum ether and then dried under vacuum over phosphorus pentoxide and potassium hydroxide. 15 g of 5,6-dimethoxy-1,3-dihydroindol-2-ylideneamine hydrochloride were obtained (yield=65%).

$^1$H and $^{13}$C NMR in accordance with the structure.

$^1$H NMR (DMSO-$d_6$; 400 MHz)

| δ (ppm) | multiplicity | integration |
|---|---|---|
| 3.73 | s | 3 |
| 3.76 | s | 3 |
| 4.09 | s | 2 |
| 6.83 | s | 1 |
| 7.11 | s | 1 |
| 9.49–9.78 | 2s | 2 |
| 11.73 | s | 1 |

Example No. 7: Preparation of 5,6-dihydroxy-1,3-dihyroindol-2-ylideneamine hydrochloride

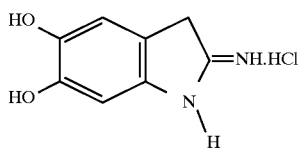

In accordance with Example No. 6, 1.9 g of (4,5-dihydroxy-2-nitrophenyl)acetonitrile were dissolved in a 20 ml/20 ml mixture of THF/37% HCl which was treated with 5 g of zinc. After treatment, 1.8 g of 5,6-dihydroxy-1,3-dihydroindol-2-ylideneamine hydrochloride were obtained (yield=90%).

$^1$H and $^{13}$C NMR in accordance with the structure.

$^1$H NMR (DMSO-$d_6$; 400 MHz)

| δ (ppm) | multiplicity | integration |
|---|---|---|
| 3.97 | s | 2 |
| 6.67 | s | 1 |
| 6.80 | s | 1 |
| 8.00–9.00 | m | 2 |
| 9.42–9.66 | 2 s | 2 |
| 11.69 | s | 1 |

FORMULATION EXAMPLES

Formulation Examples 1 and 2:

The following dye compositions were prepared (contents in grams):

| Compositions | 1 | 2 |
|---|---|---|
| 2-Imino-2,3-dihydro-1H-indol-4-ol · HBr | 1.14 | |
| 5,6-Dihydroxy-1,3-dihydroindol-2-ylideneamine · HCl | | 0.68 |
| Para-phenylenediamine | 0.54 | |
| Para-toluylenediamine | | 0.66 |
| Common dye support | () | () |
| Demineralized water qs | 100 g | 100 g |

(**): common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company Akzo | 7.0 g |
| Diethylaminopropyl laurylamino succinamate, sodium salt, containing 55% AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution, containing 35% AM | 0.455 g AM |
| Ammonium acetate | 0.8 g |
| Antioxidant, sequestering agent | qs |
| Fragrance, preserving agent | qs |
| Aqueous ammonia containing 20% $NH_3$ | 10.0 g |

Each dye composition 1 and 2 was mixed, at the time of use, with an equal weight amount of 20-volumes aqueous hydrogen peroxide solution (6% by weight).

Each mixture obtained was applied for 30 minutes to locks of natural, permanent-waved or non-permanent-waved grey hair containing 90% white hairs, at a rate of 28 g per 3 g of hair. After rinsing, washing with a standard shampoo and drying, the locks were dyed in the shades shown in Table I below:

TABLE I

| Example | 1 | 2 |
|---|---|---|
| Shade obtained on natural grey hair containing 90% white hairs | Iridiscent mahogany-dark blond | Ash-beige light blond |
| Shade obtained on permanent-waved grey hair containing 90% white hairs | Coppery-mahogany-light chestnut | Golden-ash natural dark blond |

We claim:

1. A composition for dyeing keratin fibres comprising
at least one coupler selected from 2-iminoindoline derivatives of formula (I) or acid addition salts thereof:

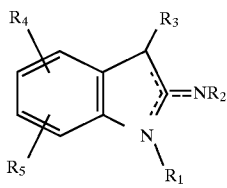

wherein:
$R_1$ represents a hydrogen atom, a $C_1$–$C_4$ alkyl, $C_1$–$C_4$ monohydroxyalkyl, $C_2$–$C_4$ polyhydroxyalkyl or ($C_1$–$C_4$)alkoxycarbonyl radical or a $C_2$–$C_4$ acyl radical;

$R_2$ represents a hydrogen atom or a $C_1$–$C_4$ alkyl, phenyl or arylsulphonyl radical;

$R_3$ represents a hydrogen atom or a $C_1$–$C_4$ alkyl radical which may be substituted with one or more hydroxyl, $C_1$–$C_4$ alkoxy, amino, mono($C_1$–$C_4$)alkylamino, di($C_1$–$C_4$)alkylamino, cyano or aryl groups;

$R_4$ and $R_5$, which may be identical or different, represent a hydrogen atom or a hydroxyl, $C_1$–$C_4$ alkyl, $C_1$–$C_4$ alkoxy, amino, mono($C_1$–$C_4$)alkylamino, di($C_1$–$C_4$) alkylamino or $C_7$–$C_{11}$ aralkyl radical, a halogen atom or a nitro group; or 4-benzyloxy-1,3-dihydroindol-2-ylideneamine, or an acid addition salt thereof; and at least one oxidation base.

2. A composition according to claim 1 wherein said composition further comprises a medium suitable for dyeing.

3. A composition according to claim 1 wherein said keratin fibres are human keratin fibres.

4. A composition according to claim 3 wherein said human keratin fibres are hair.

5. A composition according to claim 1 wherein said at least one coupler is selected from:
4-benzyloxy-1,3-dihydroindol-2-ylideneamine,
4-methoxy-1,3-dihydroindol-2-ylideneamine,
2-imino-2,3-dihydro-1H-indol-4-ol,
5-chloro-7-methoxy-1,3-dihydroindol-2-ylideneamine,
5,6-dimethoxy-1,3-dihydroindol-2-ylideneamine,
5,6-dihydroxy-1,3-dihydroindol-2-ylideneamine,
1,3-dihydroindol-2-ylideneamine,
2-imino-2,3-dihydro-1H-indole-5,6-diol, or
acid addition salts thereof.

6. A composition according to claim 1 wherein said acid addition salts are selected from hydrochlorides, hydrobromides, sulphates, tartrates or acetates.

7. A composition according to claim 1 wherein said at least one coupler represents from about 0.0005 to 12% by weight relative to the total weight of the dye composition.

8. A composition according to claim 7 wherein said at least one coupler represents from about 0.005 to 6% by weight relative to the total weight of the dye composition.

9. A composition according to claim 1 wherein said at least one oxidation base is selected from para-phenylenediamines, bis-(phenyl)alkylenediamines, para-aminophenols, ortho-aminophenols, heterocyclic bases, or acid addition salts thereof.

10. A composition according to claim 1 wherein said at least one oxidation base represents from about 0.0005 to 12% by weight relative to the total weight of the dye composition.

11. A composition according to claim 10 wherein said at least one oxidation base represents from about 0.005 to 6% by weight relative to the total weight of the dye composition.

12. A composition according to claim 1 wherein said composition further comprises at least one additional ingredient selected from couplers or direct dyes.

13. A composition according to claim 2 wherein said medium suitable for dyeing comprises water.

14. A composition according to claim 13 wherein said medium comprises a mixture of water and at least one organic solvent selected from $C_1$–$C_4$ lower alkanols, glycerol, glycols, glycol ethers, or aromatic alcohols.

15. A composition according to claim 1 wherein said composition has a pH ranging from 3 to 12.

16. A composition according to claim 1 wherein said composition is in the form of liquids, creams or gels or any other form which is suitable for dyeing keratin fibres.

17. A composition according to claim 16 wherein said keratin fibres are human hair.

18. A process for preparing a composition for the oxidation dyeing of keratin fibres comprising the step of including in said composition at least one coupler according to claim 1 in combination with at least one oxidation base.

19. A process according to claim 18 wherein said keratin fibres are human keratin fibres.

20. A process according to claim 19 wherein said human keratin fibres are hair.

21. A process for the oxidation dyeing of keratin fibers comprising the steps of applying to said fibers a dye composition according to claim 1, and applying to said fibers an oxidizing agent in order to develop a color at an acidic, neutral or alkaline pH.

22. A process according to claim 21 wherein said keratin fibres are human keratin fibres.

23. A process according to claim 22 wherein said human keratin fibres are hair.

24. A process according to claim 21 wherein said oxidizing agent is combined with said dye composition at the time of application and thereafter said dye composition and said oxidizing agent are applied to said fibres.

25. A process according to claim 21 wherein said dye composition is applied to said fibres and thereafter said oxidizing agent is applied to said fibres.

26. A process according to claim 21 wherein said oxidizing agent is applied to said fibres and thereafter said dye composition is applied to said fibres.

27. A process according to claim 21 wherein said oxidizing agent and said dye composition are separately and simultaneously applied to said fibres.

28. A process according to claim 21 wherein said oxidizing agent is present in an oxidizing composition that is applied to said fibres and thereafter said dye composition is applied to said fibres.

29. A process according to claim 21 wherein said oxidizing agent is present in an oxidizing composition that is applied to said fibres after said dye composition is applied to said fibres.

30. A process according to claim 21 wherein said oxidizing agent is present in an oxidizing composition that applied to said fibres separately from and simultaneously with said dye composition.

31. A process according to claim 21 wherein said oxidizing agent is selected from hydrogen peroxide, urea peroxide, alkali metal bromates, or persalts.

32. A process according to claim 31 wherein said persalts are selected from perborates or persulphates.

33. A multi-compartment device or multi-compartment dyeing kit comprising a first compartment containing a dye composition according to claim 1, and a second compartment containing an oxidizing composition.

* * * * *